(12) United States Patent
Coute et al.

(10) Patent No.: US 7,256,052 B2
(45) Date of Patent: Aug. 14, 2007

(54) CHEMICAL REACTION AND ANALYSIS SYSTEM

(75) Inventors: Nicolas P. Coute, Houston, TX (US); John K. Pierce, Houston, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 644 days.

(21) Appl. No.: 10/273,765

(22) Filed: Oct. 18, 2002

(65) Prior Publication Data
US 2004/0077102 A1   Apr. 22, 2004

(51) Int. Cl.
*G01N 1/22* (2006.01)
(52) U.S. Cl. .................. 436/181; 422/99; 422/100; 73/23.2; 73/23.41; 436/180
(58) Field of Classification Search .......... 422/99–100; 436/180–181; 73/23.2, 23.41
See application file for complete search history.

(56) References Cited

U.S. PATENT DOCUMENTS

| 4,043,202 | A |   | 8/1977  | Etheridge ............ 73/422 |
| 4,988,626 | A |   | 1/1991  | Ajot et al. ........... 436/148 |
| 5,102,628 | A |   | 4/1992  | De Lasa ............. 422/140 |
| 5,376,335 | A |   | 12/1994 | Gleaves ............. 422/80 |
| 6,652,625 | B1 | * | 11/2003 | Tipler et al. .......... 95/82 |
| 2001/0051110 | A1 |   | 12/2001 | Borade et al. ........ 422/99 |
| 2003/0175173 | A1 | * | 9/2003  | Karlsson et al. ...... 422/130 |

FOREIGN PATENT DOCUMENTS

| FR | 2 777 805 A1 | 10/1999 |
| GB | 2 124 369 | 2/1984 |
| WO | WO98/07026 | 2/1998 |
| WO | WO99/60396 | 11/1999 |

OTHER PUBLICATIONS

Ind. Eng. Chem. V57 N.1.18-25, "An Automatic Precision Microreactor," pp. 18-21 (Jan. 1965).
J. Chromatogr. 119, 620-4, A Dual-Channel Micro-Reactor for Reaction Gas Chromatography, pp. 620 (1976).
J. Chromatogr. 81(2), 207-32 "Studies on Catalysts and Catalysis by the Techniques of Gas Chromatography," pp. 222 (1973).
J. Chromatogr. 243(2), 279-84 "Four-reactor apparatus for chromatographic studies of catalysts and sorbents," p. 281 (1982).
Lausanne. Chem.Eng. J., A continuous microreactor system with gas chromatograph for studying combustion of hydrocarbons, pp. 111-113 (1982).
1988 AICHE Spring Natl. Meet. (New Orleans Mar. 6-10, 1988) Prepr. N.54B 8P, Design of a Dual Microreactor System for Screening Novel Catalysts.
Creer, J.G. et al, *"The Design and Construction of a Multichannel Microreactor for Catalyst Evaluation"*, Applied Catalysis, vol. 22, No. 1, 1986, pp. 85-95, XP008013710 (Elsevier Science Publishers B.V., Amsterdam, NL).
Abstract, FR 2 777 805 A1, published Oct. 29, 1999.

* cited by examiner

*Primary Examiner*—Jill Warden
*Assistant Examiner*—Jyoti Nagpaul

(57) ABSTRACT

This invention is to a microreactor type of reaction and analysis system. The system includes a chemical reaction chamber having internal conduits through which a chemical reactant, such as a reaction gas, can be fed. The conduits for transporting fluids such as reactant, carrier gas and balance gas are in appropriate communication such that the amount of reactant going directly to a catalyst located in the reaction chamber can be optimally controlled. The system is highly useful for studying the kinetics of a chemical reaction.

8 Claims, 5 Drawing Sheets

CHEMICAL REACTION AND ANALYSIS SYSTEM

FIELD OF THE INVENTION

This invention is directed to a chemical reaction and analysis system. In particular, this invention is to a microreactor type of reaction and analysis system.

BACKGROUND OF THE INVENTION

Microreactor systems are typically used to measure catalytic activity. One conventional type of microreactor system is a pulse unit. A pulse unit is one in which a micro or nano scale reaction sample is injected into a micro or nano scale type of chemical reaction unit which contains a catalyst. Upon contact with the catalyst, the reactant is converted into a chemical reaction product, and the product is sent to an analyzer for analysis.

A pulse unit typically includes a syringe type of injector for injecting the chemical reactant into the unit. In order to transport the reactant into the reaction chamber where the catalyst is located, a carrier gas is used. The carrier gas is essentially operated as a steady flow of inert gas that is in fluid communication with the catalyst in the reaction chamber. As the carrier gas flows through the reaction chamber, the reactant is injected by the syringe into a common conduit with the carrier gas, and the carrier gas transports the reactant to the reaction zone for contact with the catalyst. This type of injection process is referred to as a pulse technique, since only pulses of reactant can be injected into the reaction chamber, as opposed to a steady or continuous flow of reactant at a known concentration.

UK Patent Application GB 2 124 369 A discloses a pulse type of microreactor system. The system is provided for use in refining, petrochemistry, treatment of synthesis gas or fine chemistry. The system includes a fixed bed catalyst reactor, means for injecting a charge of material into the reactor with the aid of a carrier gas, a furnace capable of heating to a range of from 50° C. to 300° C., a plurality of sampling valves, and means for analyzing reaction product.

A problem with pulse type microreaction units is generally that it is difficult to control reaction conditions such that various reaction parameters can be studied with reliable accuracy. For example, kinetic studies require that pressure and conversion be easily controlled and monitored. In units such as pulse units, reaction pressure and conversion is not easily controlled due to the pulse type nature of the reactant being pushed through a conversion catalyst. If one is trying to measure, for example, kinetics at less than 100% conversion, one may have to use many pulses as an estimate of the catalyst activity. This is because a typical pulse quantity of reactant encountering fresh catalyst will typically have 100% conversion due to the micro or nano scale quantity of the pulse sample that is typically injected into the reaction unit. It is, therefore, desirable to find reaction units, particularly micro scale or nano scale injection units, which are suitable for kinetic studies.

SUMMARY OF THE INVENTION

This invention allows for kinetic study of chemical reactions at very small scale. The system of the invention allows for continuous feed of reactant without the need to transport the reactant to the reaction chamber using a carrier gas. Instead, the system of the invention utilizes a carrier gas as a means to recover the reaction product from the reaction chamber, and send the reaction product to an analysis unit.

In one embodiment, the invention provides a chemical reaction chamber. The chemical reaction chamber comprises a reaction zone in fluid connection with a reaction zone inlet and a reaction zone outlet; a reaction gas transport zone in fluid connection with the reaction zone inlet, the reaction gas transport zone having a reaction gas inlet and a reaction gas outlet; a balance gas injector extending into the reaction gas transport zone; and a carrier gas transport zone in fluid communication with the reaction zone outlet, the carrier gas transport zone having a carrier gas inlet and a carrier gas outlet.

In another embodiment, the reaction zone inlet and the reaction gas inlet are in fluid communication with one another so that fluid can flow from the reaction gas inlet through the reaction gas transport zone and the reaction zone inlet, and to the reaction zone. Desirably, the reaction zone outlet and the carrier gas outlet are in fluid communication with one another so that fluid can flow from the reaction zone, through the reaction zone outlet, through the carrier gas transport zone, and out through the carrier gas outlet.

In another embodiment of the chemical reaction chamber, the reaction gas inlet and the reaction gas outlet are in fluid communication with one another so that fluid can flow from the reaction gas inlet and out through the reaction gas outlet. In addition, the carrier gas inlet and the carrier gas outlet are in fluid communication with one another so that fluid can flow from the carrier gas inlet and out through the carrier gas outlet.

In the chemical reaction chamber of the invention, it is also desirable that the carrier gas outlet, the carrier gas transport zone, and the carrier gas inlet are in connection with one another so that fluid can flow from the carrier gas inlet, through the carrier gas transport zone, and out through the carrier gas outlet while another fluid is flowed through the reaction zone, the reaction zone outlet, the carrier gas transport zone and out through the carrier gas outlet. Preferably, the balance gas injector extends into the reaction gas transport zone and on into the reaction zone inlet.

In yet another embodiment of the reaction chamber of the invention, the balance gas injector extends into the chemical reaction chamber and is in communication with the reaction zone inlet, such that fluid injected through the balance gas injector and into the chemical reaction chamber flows through the reaction zone inlet and out through the reaction gas transport zone, while another fluid flows from the reaction gas inlet through the reaction gas transport zone and out through the reaction gas outlet.

The invention further provides a chemical reaction system. The chemical reaction system comprises a fluid injector in fluid communication with a chemical reaction chamber of the invention.

Also provided in the invention is a chemical analyzer system. The chemical analyzer system comprises a fluid injector in fluid communication with a chemical reaction chamber of the invention. Further included is a chemical analyzer in fluid communication with the carrier gas outlet of the chemical reaction chamber.

One further aspect provided by the invention is a process for analyzing a chemical reaction product. The process comprises injecting a reactant into a reaction gas transport zone of a chemical reaction chamber; flowing the reactant from the gas transport zone into a reaction zone; contacting the reactant with a catalyst in the reaction zone to form a chemical reaction product; flowing a carrier gas through a carrier gas transport zone so as to contact the chemical reaction product in the carrier gas transport zone, and move the chemical reaction product out from the reaction zone and into a chemical analyzer; and analyzing the chemical reaction product in the chemical analyzer.

In another embodiment, a process for analyzing a chemical reaction product is provided which comprises flowing a reactant into and out of a reaction gas transport zone; flowing a balance gas into a reaction zone and through the reaction gas transport zone along with the injected reactant; redirecting the reactant and balance gas to go through and out of the reaction zone to contact a catalyst in the reaction zone and form a chemical reaction product; flowing a carrier gas through a carrier gas transport zone so as to contact the chemical reaction product and move the chemical reaction product out from the reaction zone and into a chemical analyzer; and analyzing the chemical reaction product in the chemical analyzer.

BRIEF DESCRIPTION OF THE DRAWINGS

Examples of various embodiments of this invention are shown in the attached drawings, wherein.

DETAILED DESCRIPTION OF THE INVENTION

Figure 1A:
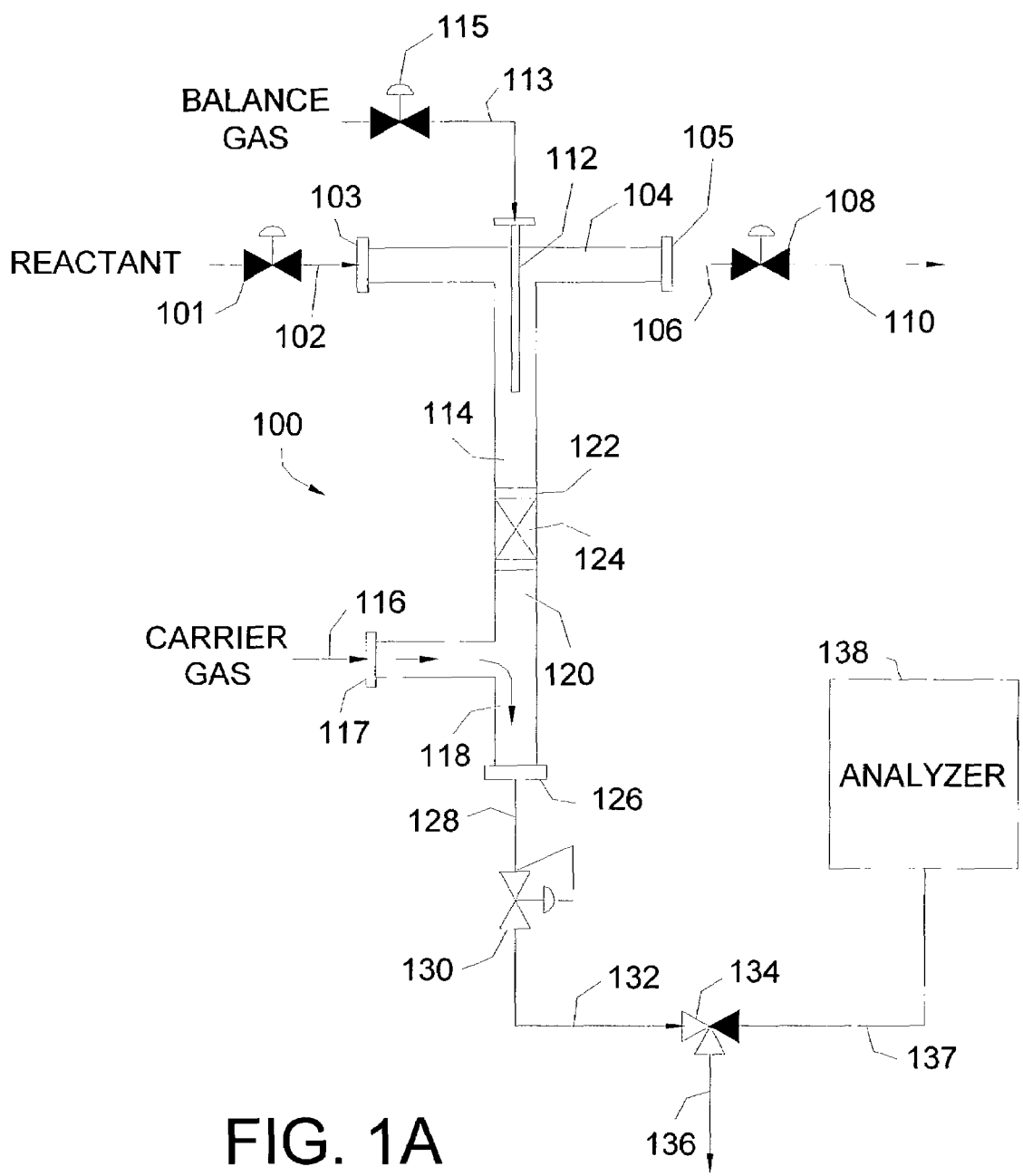
FIG. 1A shows one embodiment in a pre-reaction mode in which carrier gas flows through a reaction chamber until a predetermined pressure and/or temperature is achieved.

This invention provides a chemical reactor and analyzer system which is highly useful for studying the kinetics of a chemical reaction. The system is particularly useful, because chemical reaction studies can be performed at very small scale, e.g., micro or nano scale type reactions, with a high degree of control over reaction parameters such as temperature and pressure of reaction, as well as controlling the degree of conversion of reactant to product.

The system includes a chemical reaction chamber having internal conduits through which a chemical reactant, such as a reaction gas, can be fed. The conduits for transporting fluids such as reactant, carrier gas and balance gas are in appropriate communication such that the amount of reactant going directly to a catalyst located in the reaction chamber can be optimally controlled. For example, the amount of feed going to the catalyst in the reaction chamber can be easily quantified, because the arrangement of conduits in the reaction chamber does not require the use of a carrier gas as a motive force to carry the chemical reactant to contact the catalyst. Instead, carrier gas that is injected into the system of this invention is used to carry the chemical reaction product away from the catalyst, out of the chemical reaction chamber, and on to an analyzer unit. The arrangement of conduits within the system of this invention is such that reaction pressure and temperature can also be easily monitored and controlled, which is particularly desirable in studying chemical kinetic mechanisms.

According to the invention, a chemical reactant is injected into a chemical reaction chamber. Desirably, the chemical reactant is in the form of a vapor or gas as it goes into a reaction zone portion of the reaction chamber. A liquid or solid sample can be reacted in this invention, however, as long as the liquid or solid is vaporized prior to contacting the catalyst in the reaction zone.

Before the reactant or reaction gas enters into the reaction zone, it is passed through a reaction gas transport zone, and directed to by-pass the chemical reaction zone, until pressure and temperature conditions are stabilized. Once the appropriate reaction conditions are maintained within the chemical reaction chamber, the reactant is then directed to flow through the chemical reaction zone to contact the catalyst within the reaction zone to form a chemical reaction product. The chemical reaction product then leaves the reaction zone, and is directed to exit the chemical reaction chamber.

Prior to exiting the chemical reaction chamber, the chemical reaction product flows through a carrier gas transport zone, where the chemical reaction product contacts a flowing carrier gas. The carrier gas mixes with the chemical reaction product and applies an additional motive force to remove the chemical reaction product from the chemical reaction chamber.

A balance gas can also be injected into the chemical reaction chamber to aid in controlling direction of flow of the reactant, if desired. Desirably, the balance gas is injected into the reaction gas transport zone or at a point just before the reactant enters into the reaction zone. The balance gas can be used to further direct the reactant to by-pass the reaction zone while the system achieves appropriate conditions. By opening and/or or closing valves connected to associated conduits in fluid communication with the reaction gas transport zone and the reaction zone inlet area, flow of reactant can be appropriately controlled to by-pass or enter the reaction zone.

Once the chemical reaction product leaves the chemical reaction chamber, it is ultimately sent to a chemical analyzer. The chemical analyzer can be one of any conventional type of analyzer useful for measuring a desired characteristic of the chemical reaction product. Examples of such analyzers include gas chromatography, mass spectrometry, nuclear magnetic resonance, thermal analysis, and electro analysis type systems.

The invention is not confined to any particular kind of chemical reactant or catalyst for forming a reaction product. It is desirable, however, that the reactant be in the form of a vapor when the reactant contacts the catalyst. It is also desirable that the reaction product be recovered in the form of a vapor or at least be in a liquid state such that the liquid can be transported by the carrier gas to a chemical analysis unit. Of course, the system can include an appropriate heater unit in order to vaporize any number of reactants and reaction products so that the system will operate satisfactorily. The system is particularly useful in converting hydrocarbon reactants into hydrocarbon reaction products.

Examples of reactants which can be used in this invention include heavy and light oils, as wells as lighter hydrocarbons. Such hydrocarbons can include petroleum based hydrocarbons (including oils, distillates, and light lubes), and such hydrocarbons can contain oxygen, nitrogen or sulfur components. Examples of oxygen containing hydrocarbons include one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

The balance gas and/or the carrier gas injected into the system can be any type of vapor composition that does not react with the reactant, reaction product or catalyst contained in the reaction zone; in essence, these gases are inert to the system. Non-limiting examples of balance and/or carrier gases include helium, argon, nitrogen, carbon monoxide, carbon dioxide, water (in the form of steam), essentially non-reactive paraffins (especially alkanes such as methane, ethane, and propane), essentially non-reactive aromatic compounds, and mixtures thereof.

Catalysts which can be used in the invention are desirably solid catalysts. Any solid catalyst which can be supported in the reaction zone can be readily used. One example of a catalyst that can be used in this invention is a molecular sieve type of catalyst. Such catalysts are particularly desirable, since they can be quite easily inserted into simple reaction chamber conduits with the use of inert packing materials. Examples of molecular sieve catalysts include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

The reaction zone is desirably maintained at a temperature and pressure at which the reactant and reaction product are in the vapor phase. Desirably, the reactant is heated prior to contacting the catalyst at a temperature sufficient to have the reactant contact the catalyst in the form of a reaction gas. Any conventional means can be used to heat the reactant, and heating can be performed external or internal to the chemical reaction chamber. It is desirable to heat the reactant to a temperature of at least 50° C., preferably to a temperature of from about 100° C. to about 800° C. The temperature should not be so high, however, such that undesired byproduct reactions, e.g., thermal degradation, occurs.

One embodiment of the chemical reaction chamber of the invention is shown in FIGS. 1A-D. As shown in FIGS. 1A-D, a chemical reaction chamber 100 is comprised of a reaction zone 122 in fluid connection with a reaction zone inlet 114 and a reaction zone outlet 120. The reaction zone 122 can include a reaction medium or catalyst 124.

In fluid connection with the reaction zone inlet 114 is also a reaction gas transport zone 104. The reaction gas transport zone 104 has a reaction gas inlet 103 and a reaction gas outlet 105.

The chemical reaction chamber 100 further includes a balance gas injector 112 which extends into the reaction gas transport zone. A carrier gas transport zone 118 is also shown in fluid communication with the reaction zone outlet 120. The carrier gas transport zone 118 further includes a carrier gas inlet 117 and a carrier gas outlet 126.

The chemical reaction chamber 100 can be used as a part of a chemical reaction system or an analyzer system. In the embodiment shown in FIGS. 1A-D, an analyzer 138 is shown connected to the chemical reaction chamber 100 by way of a line 128, a back pressure regulator 130, a line 132, a 3-way valve 134, and a line 137.

FIG. 1A shows a series of valves 101, 115, 108 and 134 in various closed and open positions to reflect what is referred to herein as a pre-reaction mode. In the pre-reaction mode, the 3-way valve is arranged so that carrier gas is allowed to pass through a line 116 and enter the chemical reaction chamber 100 through the carrier gas inlet 117. The carrier gas passes through the carrier gas inlet 117, through the carrier gas transport zone 118, and out of the chemical reaction chamber 100 through the carrier gas outlet 126.

In the pre-reaction mode, the carrier gas leaves the chemical reaction chamber 100, passing through the line 128, the back pressure regulator 130, and the line 132 to the 3-way valve 134. The 3-way valve is open so that the carrier gas passes to a line 136 and on to a vent or suitable container.

As seen in FIG. 1A, valve 101 is closed to prevent any reactant or reaction gas from entering the chemical reaction chamber 100 during the pre-reaction mode. Valve 115 is also closed to prevent entry of balance gas, and valve 108 is closed so that the carrier gas will exit the chemical reaction chamber 100 through the carrier gas outlet 126 only. The back pressure regulator 130 is operated so as to attain the desired pressure in the reaction chamber 100 during the pre-reaction mode.

Figure 1B:
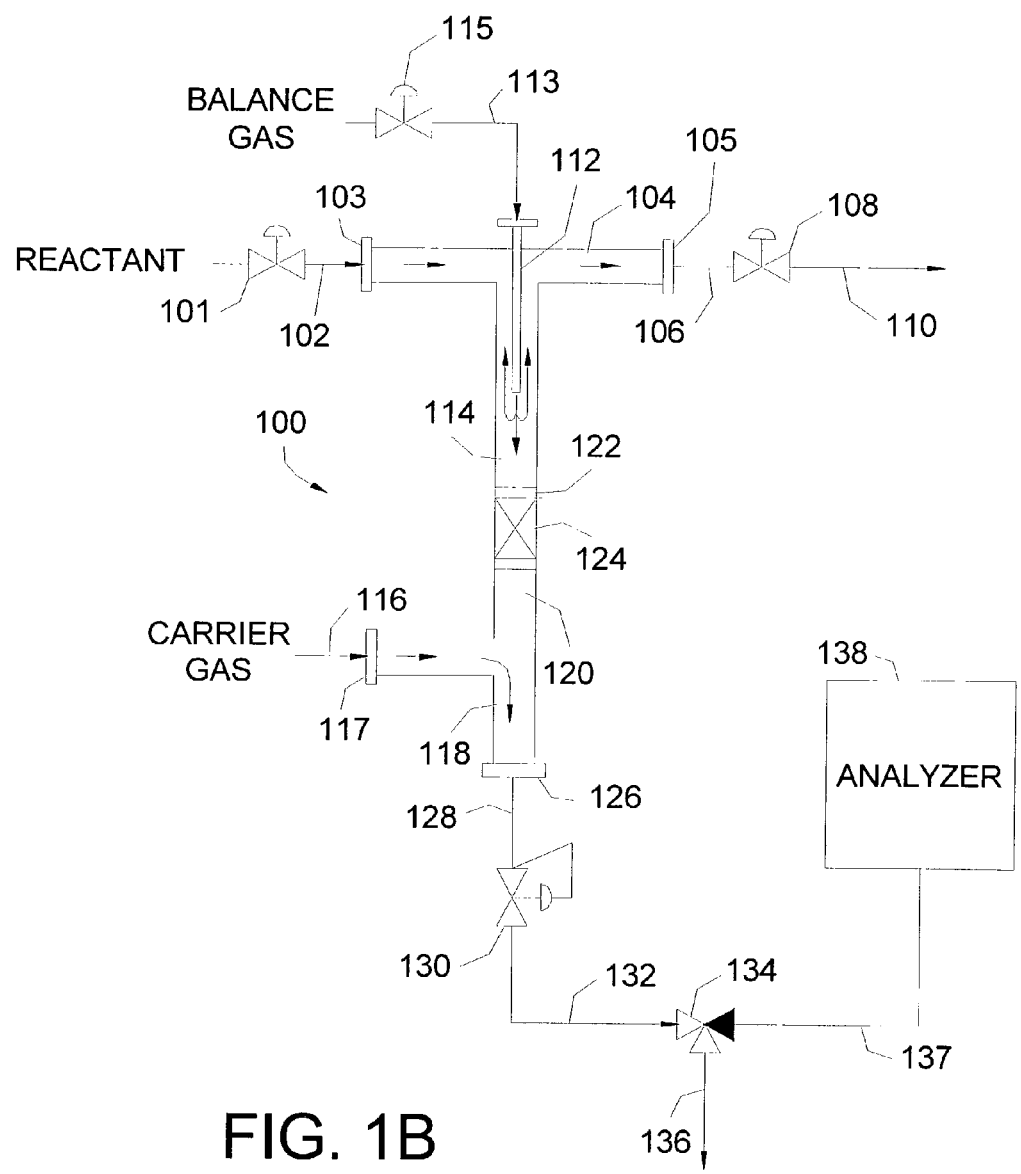
FIG. 1B shows the embodiment of FIG. 1A in a by-pass or initializing mode in which reactant or reaction gas and balance gas by-pass the reaction zone as temperature and/or pressure conditions are initialized.

FIG. 1B shows the embodiment in the by-pass or initializing mode. In the by-pass mode, valve 101 is open so that reactant or reaction gas passes through a line 102, and enters the chemical reaction chamber 100 through the reaction gas inlet 103.

In the by-pass mode, valve 108 is also in the open position so that the reaction gas passes through the reaction gas transport zone 104, and out the chemical reaction chamber 100 through the reaction gas outlet 105. Since valve 108 is in the open position, the reaction gas continues through a line 106, through the valve 108, and on to a vent or suitable container.

So as to further aid in maintaining the reaction gas in the by-pass mode, i.e., keep the reaction gas from passing through the reaction zone 122, a balance gas is injected through a line 113 and the balance as injector 112. The balance gas injector 112 is placed in the chemical reaction chamber 100 so that the balance gas prevents the reaction gas from passing through the reaction zone 122. The balance gas injector 112 needs, therefore, to extend into the reaction gas transport zone to provide such a function. The embodiment in FIG. 1B, however, further shows the balance gas injector extending into the reaction gas transport zone and on into the reaction zone inlet to further ensure that the reaction gas does not enter the reaction chamber 122.

The balance gas can also be used to assist in initializing the pressure of the chemical reaction chamber 100. Since the valve 108 is now open, the pressure set by the back pressure regulator 130 in the pre-reaction mode will decrease. Opening the valve 108 creates a drop in pressure in the system. Therefore, to counter a loss of pressure, the balance gas can be injected at an increasing pressure until the pressure in the reaction chamber 100 is balanced to that previously set by the back pressure regulator 130 in the pre-reaction mode.

Figure 1C:
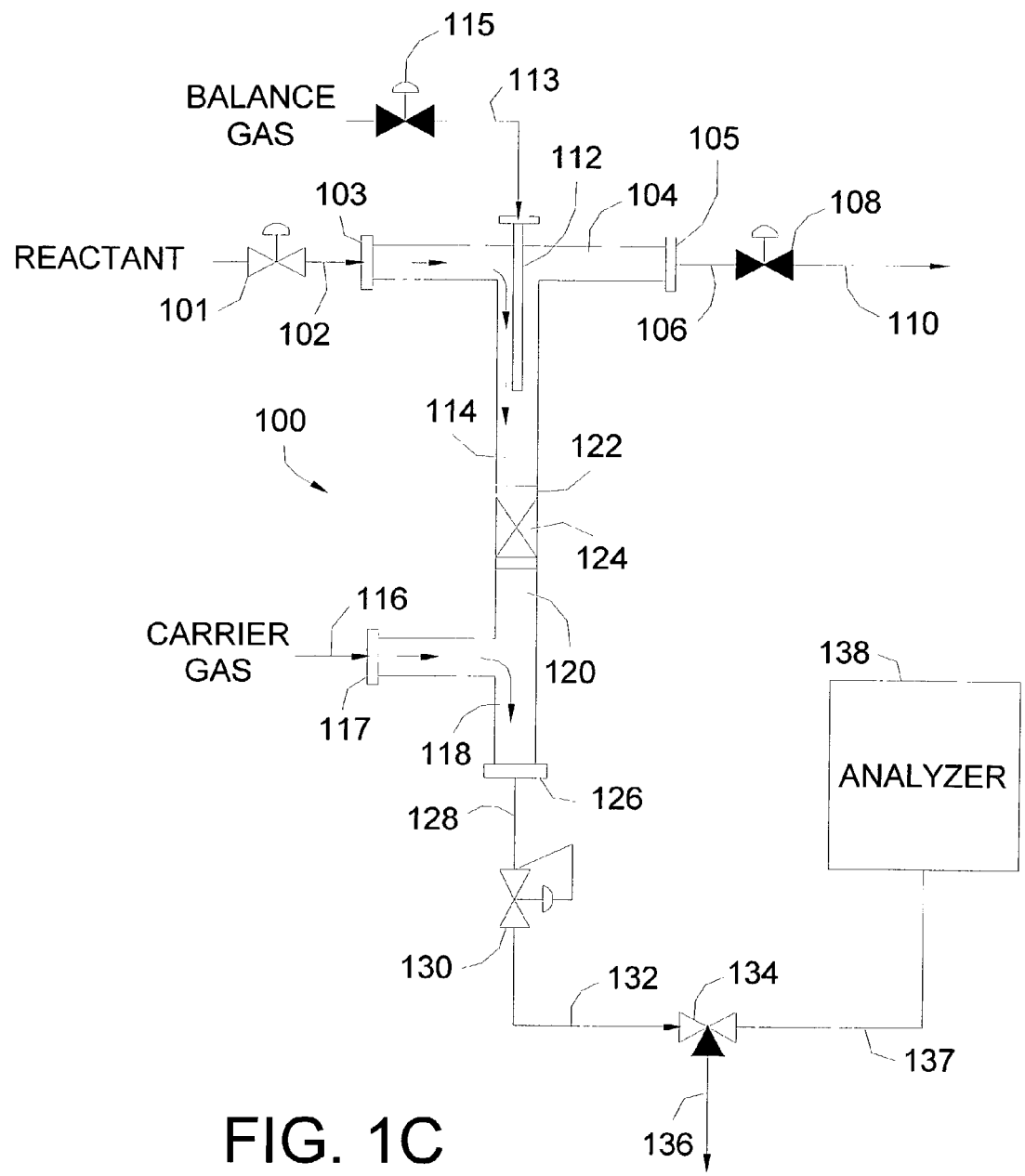
FIG. 1C shows the embodiment of FIG. 1A in a reaction mode in which reaction gas flows through a reaction zone of the reaction chamber.

FIG. 1C shows the chemical reaction chamber 100 operating in the reaction mode. In the reaction mode, valve 108 and valve 115 are closed. This action redirects the reaction gas to flow from the reaction gas transport zone 104 to the reaction zone 122. In passing through the reaction zone 122, the reactant contacts reaction medium or catalyst 124, which converts the reactant to a chemical reaction product.

The chemical reaction product passes from the reaction zone 122 to the reaction zone outlet 120, and then to the carrier gas transport zone 118. In the carrier gas transport zone 118, the chemical reaction product contacts the flowing carrier gas, which acts to move the chemical reaction product out from the chemical reaction zone.

The chemical reaction product and carrier gas exit the chemical reaction chamber 100 through the carrier gas outlet 126. The chemical reaction product and carrier gas pass through the line 128, the back pressure valve 130, the line 132 and through the 3-way valve 134. The 3-way valve is opened so that the gases pass through the line 137 to enter the analyzer 138, where analysis of the chemical reaction product takes place.

Figure 1D:
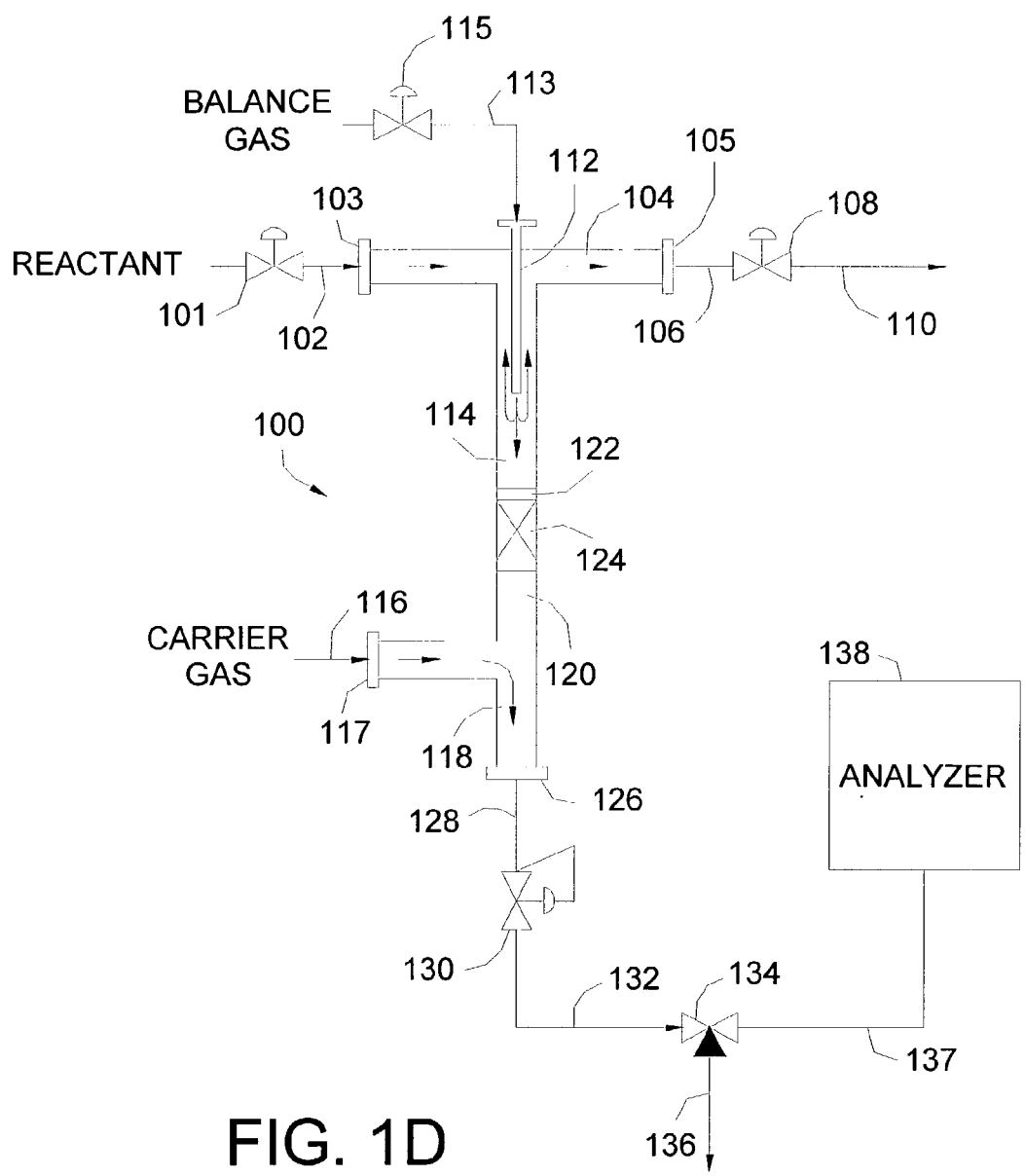
FIG. 1D shows the embodiment of FIG. 1A in a shut-off mode in which balance gas directs the reactant gas away from the reaction zone.

FIG. 1D shows the chemical reaction chamber 100 in the shut-off mode. In the shut-off mode, valves 115 and 108 are opened. This allows balance gas to enter the chemical reaction chamber 100, and causes the reactant or reaction gas to be redirected to flow out of the chemical reaction chamber 100 through the reaction gas outlet 105. In the shut-off mode the reaction gas no longer flows through the reaction zone 122 so that the chemical reaction process is effectively shut-off.

Figure 2:
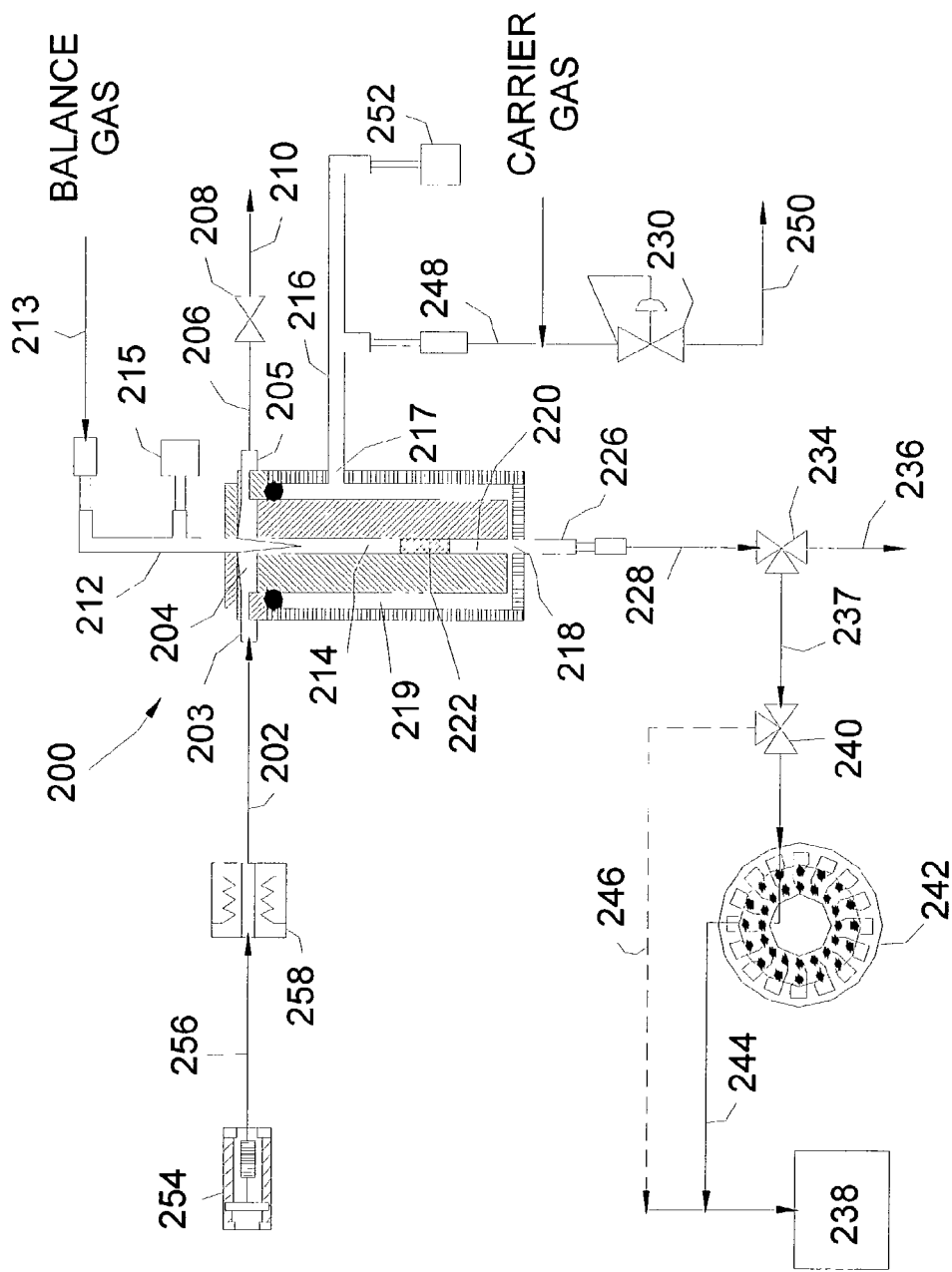
FIG. 2 shows one embodiment of a system of the invention in which a liquid is used as the reactant.

FIG. 2 shows one embodiment of an analyzer system according to the invention. In this embodiment, a chemical reaction chamber 200 is incorporated which operates substantially the same as that described in FIGS. 1A-D. However, in the chemical reaction chamber 200, a carrier gas is injected into the chemical reaction chamber 200 by way of carrier gas inlet 217 into a carrier gas chamber 219 which encircles an inner peripheral portion of the chemical reaction chamber 200. From the carrier gas chamber 219, carrier gas passes through a carrier gas transport zone 218, and out through the chemical reaction chamber 200 by way of a carrier gas outlet 226.

In the embodiment shown in FIG. 2, the pressure in reaction zone 222 is controlled by a pressure regulator valve 230. This pressure can be monitored by way of a pressure measurement device 252 connected to the chemical reaction chamber 200 by way of a line 216.

In the embodiment shown in FIG. 2, chemical reactant is inserted in liquid form to a fluid injector 254. The fluid injector 254 is capable of continuously injecting the reactant for appropriate kinetic studies.

The liquid chemical reactant, is passed through fluid injector 254 through a line 256 into a heater 258. In the heater 258, the liquid reactant is vaporized and passed through a line 202 to a reaction gas inlet 203.

In the by-pass mode, the reaction gas passes through a reaction gas transport zone 204 and out of the chemical reaction chamber 200 by way of reaction gas outlet 205. The reaction gas then passes through a line 206, across a valve 208, and through a line 210 to a vent or collection unit (not shown).

FIG. 2 also includes an optional balance gas injector 212, inserted into the chemical reaction chamber 200 through the reaction transport zone 204 and into a reaction zone inlet 214. Balance gas is injected into the balance gas injector 212 by way of a line 213, and into the reaction zone inlet 214. Line 213 is also in fluid communication with a pressure measurement device 215, which is used to measure the pressure of the system before the reaction zone 222.

In the by-pass mode, the balance gas mixes with the reaction gas in the reaction gas transport zone 204. Since valve 208 is in the open position in the by-pass mode, the gases are directed to exit the chemical reaction chamber 200 by way of the reaction gas outlet 205.

In the reaction mode, the reaction gas passes through the reaction zone inlet 214 and into the reaction zone 222, which includes a catalyst in this embodiment. As the reaction gas contacts the catalyst in the reaction zone 222, a chemical reaction product is formed. The chemical reaction product passes into a reaction zone outlet 220 and into a carrier gas transport zone 218.

In the carrier gas transport zone 218, the chemical reaction product is further propelled by the carrier gas, both passing through a carrier gas outlet 226. The chemical reaction product passes from the carrier gas outlet 226 through a line 228, and on through a 3-way valve 234. The 3-way valve 234 directs the product through a line 236 to a collection unit (not shown), or through a line 237 to another 3-way valve 240.

In typical reaction mode operation, the 3-way valve 240 is controlled so as to pass the chemical reaction product to a multi-port collection valve 242. In the multi-port collection valve 242, discrete portions of the chemical reaction product are collected, and later sent through a line 244, and on to a chemical analyzer 238 for analysis of each discrete sample.

The analyzer system in FIG. 2 also includes an optional by-pass line 246. This by-pass line 246 can be used to send chemical reaction product or carrier gas to a variety of ports and/or connections, by-passing the multi-port collection valve 242. If desired, the by-pass line 246 can be linked in direct fluid communication with chemical analyzer 238.

Having now fully described this invention, it will be appreciated by those skilled in the art that the invention can be performed within a wide range of parameters within what is claimed, without departing from the spirit and scope of the invention.

The invention claimed is:

1. A process for analyzing a chemical reaction product, comprising:

flowing a reactant into and out of a reaction gas transport zone through a reaction gas transport zone outlet;

flowing a balance gas into a reaction zone such that said balance gas prevents said reactant from flowing into said reaction zone, said balance gas flowing through the reaction gas transport zone along with the injected reactant;

redirecting the reactant and balance gas to go through and out of the reaction zone to contact a catalyst in the reaction zone and form a chemical reaction product;

flowing a carrier gas through a carrier gas transport zone so as to contact the chemical reaction product and move the chemical reaction product out from the reaction zone and into a chemical analyzer; and analyzing the chemical reaction product in the chemical analyzer.

2. The process of claim 1, wherein the reaction zone inlet and the reaction gas inlet are in fluid communication with one another so that fluid can flow from the reaction gas inlet through the reaction gas transport zone and the reaction zone inlet, and to the reaction zone.

3. The process of claim 1, wherein the reaction zone outlet and the carrier gas outlet are in fluid communication with one another so that fluid can flow from the reaction zone, through the reaction zone outlet, through the carrier gas transport zone, and out through the carrier gas outlet.

4. The process of claim 1, wherein the reaction gas inlet and the reaction gas outlet are in fluid communication with one another so that fluid can flow from the reaction gas inlet and out through the reaction gas outlet.

5. The process of claim 1, wherein the carrier gas inlet and the carrier gas outlet are in fluid communication with one another so that fluid can flow from the carrier gas inlet and out through the carrier gas outlet.

6. The process of claim 1, wherein the carrier gas outlet, the carrier gas transport zone, and the carrier gas inlet are in connection with one another so that fluid can flow from the carrier gas inlet, through the carrier gas transport zone, and out through the carrier gas outlet while another fluid is flowed through the reaction zone, the reaction zone outlet, the carrier gas transport zone and out through the carrier gas outlet.

7. The process of claim 1, wherein the balance gas injector extends into the chemical reaction chamber and is in communication with the reaction zone inlet, such that fluid injected through the balance gas injector and into the chemical reaction chamber flows through the reaction zone inlet and out through the reaction gas transport zone, while another fluid flows from the reaction gas inlet through the reaction gas transport zone and out though the reaction gas outlet.

8. The process of claim 1, wherein a multi-port collection valve is disposed between the chemical analyzer and the carrier gas outlet.

\* \* \* \* \*